United States Patent [19]

Renga

[11] 4,447,650
[45] May 8, 1984

[54] METHYLENE COUPLING OF AROMATICS

[75] Inventor: James M. Renga, Midland, Mich.

[73] Assignee: The Dow Chemical Company, Midland, Ohio

[21] Appl. No.: 401,768

[22] Filed: Jul. 26, 1982

[51] Int. Cl.³ .................. C07C 41/18; C07C 37/11; C07C 17/00
[52] U.S. Cl. .................. 568/640; 568/638; 568/723; 568/931; 560/101; 570/191; 570/199; 585/425
[58] Field of Search .............. 570/194, 199, 191; 585/426, 425; 568/640, 638, 931, 723; 560/101

[56] References Cited

U.S. PATENT DOCUMENTS 3,714,280  1/1973  Stapp .................. 585/426

OTHER PUBLICATIONS

C. M. Welch et al., J.A.C.S. 73, 4391 (1951).
G. Casiraghi et al., Synthesis, 143 (1981).
L. I. Belen'kii et al., Russ. Chem. Rev., 46, 891 (1977).
Brown et al., J.A.C.S., vol. 75 (1953), 6292–6295.
Belen'kii et al., Russ. Chem. Rev. 46(9) [1977] 891–903.

*Primary Examiner*—Bernard Helfin
*Attorney, Agent, or Firm*—Douglas N. Deline

[57] ABSTRACT

Methylene coupled aromatic compounds are prepared by contacting an aromatic reactant having a reactive hydrogen with chloromethyl methyl carbonate at a temperature from about 25° C. to about 250° C. in the presence of a catalytic amount of a Lewis acid.

9 Claims, No Drawings

METHYLENE COUPLING OF AROMATICS

The present invention relates to a novel method for preparing methylene coupled aromatic compounds. More particularly, the present invention concerns a process of coupling aromatic moieties with one or more methylene linking moieties to prepare bisaryl methane compounds as well as oligomeric or polymeric compounds such as novolac resins. Bisaryl methanes, particularly bisphenol methanes are widely used as antioxidants and stabilizers for materials such as organic polymers, petroleum products, rubbers and foods.

BACKGROUND OF THE INVENTION

It is already known to prepare bisaryl methane compounds by the reaction of alkyl-substituted benzenes with paraformaldehyde in the presence of an acid catalyst such as sulfuric acid, C. M. Welch et al., *J.A.C.S.*, 73, 4391 (1951). G. Casiraghi et al., *Synthesis*, 143 (1981) additionally disclosed a similar reaction between paraformaldehyde and phenols in the presence of an acid catalyst. It is also known that small amounts of bisaryl methanes are formed as by-products in the chloromethylation of aromatic compounds, L. I. Belen'kii et al., *Russ. Chem. Rev.*, 46, 891 (1977).

SUMMARY OF THE INVENTION

According to the present invented process, methylene coupled aromatic compounds are prepared by contacting an aromatic reactant of the formula:

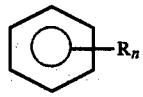

with chloromethyl methyl carbonate at a temperature from about 25° C. to about 250° C. in the presence of a catalytic amount of a Lewis acid. In the formula provided, R each occurrence may be hydrogen, halogen, nitro, hydroxyl or an alkyl, alkoxy, aryl, aralkyl, haloalkyl, alkoxycarbonyl or aroxy group of up to about 12 carbons, and n is an integer from one to four.

DETAILED DESCRIPTION OF THE INVENTION

Aromatic reactants preferably reacted with chloromethyl methyl carbonate according to the invented process include benzene, phenol and such compounds further substituted with methyl, ethyl, halo, methoxy, phenoxy or methoxycarbonyl groups. Examples include toluene, orthoxylene, metaxylene, paraxylene, mesitylene, paraethyl toluene, methoxybenzene, chlorobenzenes, chlorinated phenols, methyl salicylate, etc. Phenol reacts under the present invented process to give primarily resin, e.g., a phenol formaldehyde or novolac resin. Benzene, alkylbenzenes and substituted phenols yield primarily bisaryl methylene compounds. While any amount of aromatic reactant may be employed, it is preferred to use about equal stoichiometric amounts compared to chloromethyl methyl carbonate or a slight excess of aromatic reactant up to about 10 percent based on equivalents of chloromethyl methyl carbonate.

Chloromethyl methyl carbonate is a known compound that is readily prepared by several common techniques. Suitable processes include the radical chlorination of dimethyl carbonate with chlorine or the reaction of dimethyl carbonate with sulfuryl chloride taught by A. Kling et al., *Compt. Rend.* 170, 111–113, 234–236 (1920) (CA 14:1304), and O. Unger et al., Ger. Offen. No. 1,203,796, respectively. Any suitable process for preparing the chloromethyl methyl carbonate may be employed according to the invented process.

The reaction may be carried out at any temperature within the above-identified range but is preferably conducted within the range of about 90° C. to about 150° C. Reaction times may vary from several minutes to hours depending on the reaction conditions and phenol reactants employed.

The catalyst employed is a Lewis acid. Suitable catalysts include halogen salts of tin, zinc, iron, aluminum, etc. Preferred halogen salts are the chlorides of tin, zinc and iron. The catalyst is present in a catalytically effective amount. Suitably from about 0.1 mole percent to about 20 mole percent of the catalyst is used. Preferred amounts are between about 1 mole percent and 10 mole percent.

The process may be conducted neat or in the presence of a suitable solvent. Any inert organic liquid may be employed as a solvent. Included are hydrocarbons such as alkanes, cycloalkanes, aromatic and haloaromatic compounds, (poly)glycols, (poly)glycol ethers, alkanols, alkyl carbonates and alkylene carbonates. An excess of aromatic reactant is normally employed when no inert solvent is present.

The reaction is conducted in either a batch or continuous manner by contacting the two reactants in the presence of the catalyst and heating to the desired temperature. In addition to the desired bisaryl methane or novolac resin product, carbon dioxide, water and methyl chloride are prepared by the process. After reaction for the desired period, the crude product is separated from water formed by the process, and unreacted starting materials and solvent are removed by distillation. Further purification if desired may be by recrystallization, further distillation or any other suitable technique.

The reaction may be conducted in vessels of ordinary design and construction. Suitable reaction vessels include those of glass, steel, stainless steel, glass-lined metal, etc.

SPECIFIC EMBODIMENTS

Having described the invented process, the following examples are provided as further illustrative and are not to be construed as limiting.

EXAMPLE 1

Mesitylene (30 g, 0.25 mole), chloromethyl methyl carbonate (6.23 g, 0.05 mole) and zinc chloride (0.34 g, 0.0025 mole) were combined in a glass flask and heated to 120° C. After 5 hours, heating was discontinued, the organic layer was separated from water and dried over MgSO$_4$. Removal of excess mesitylene on a rotary evaporator gave 11.0 g of a solid. Recrystallization from hexane gave 9.8 g (78 percent yield) of bis(2,4,6-trimethylphenyl)methane, m.p. 133° C.–134° C.

EXAMPLES 2–11

The reaction conditions of Example 1 were substantially repeated employing various aromatic reactants, solvents and 5 mole percent of the catalysts further described in Table I. In all examples, the reaction product was the corresponding bisaryl methane coupled product or isomeric products.

TABLE I

| Example | ArH | moles ArH:CMMC[a] | Solvent | Catalyst | Temp °C. | Time (hr) | % Yield ArCH$_2$Ar |
|---|---|---|---|---|---|---|---|
| 2 | mesitylene | 0.25:0.05 | — | SnCl$_4$ | 120 | 20 | 77 |
| 3 | mesitylene | 0.1:0.065 | DMC[b] | ZnCl$_2$ | 95 | 54 | 44 |
| 4 | toluene | 0.25:0.05 | — | ZnCl$_2$ | 100 | 66 | 68[c] |
| 5 | methoxybenzene | 0.25:0.05 | — | ZnCl$_2$ | 100 | 20 | 65[c] |
| 6 | methoxybenzene | 0.25:0.05 | — | FeCl$_3$ | 100 | 18 | 62[c] |
| 7 | o-methylphenol | 0.10:0.05 | DMC[b] | ZnCl$_2$ | 95 | 24 | 62[d] |
| 8 | 2,6-dimethylphenol | 0.10:0.05 | toluene[e] | ZnCl$_2$ | 100 | 48 | 45 |
| 9 | 2,6-dimethylphenol | 0.10:0.05 | p-dioxane[e] | ZnCl$_2$ | 100 | 64 | 58 |
| 10 | 2,6-dimethylphenol | 0.10:0.05 | heptane[e] | ZnCl$_2$ | 100 | 22 | 42 |
| 11 | 2,6-dimethylphenol | 0.25:0.05 | — | ZnCl$_2$ | 120 | 5 | 68 |

[a]CMMC = chloromethyl methyl carbonate
[b]dimethyl carbonate, 0.15 mole
[c]mixture of three possible isomers
[d]mixture of several isomers
[e]50 ml

EXAMPLE 12

If phenol is reacted with chloromethyl methyl carbonate substantially according to the procedure of Examples 1-11, the reaction product is a novolac resin.

What is claimed is:

1. A process for preparing methylene coupled aromatic compounds comprising contacting an aromatic compound of the formula:

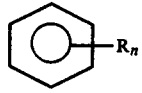

where R is independently each occurrence hydrogen, halogen, nitro, hydroxyl, or an alkyl, alkoxy, aryl, aralkyl, haloalkyl, alkoxycarbonyl or aroxy group of up to about 12 carbons; and n is an integer from one to four, with chloromethyl methyl carbonate at a temperature from about 25° C. to about 250° C., in the presence of a catalytic amount of a Lewis acid.

2. The process of claim 1 wherein the Lewis acid is a halogen salt of tin, zinc, iron or aluminum.

3. The process of claim 2 wherein the Lewis acid is SnCl$_4$, ZnCl$_2$ or FeCl$_3$.

4. The process of claim 1 wherein from about 0.1 mole percent to about 20 mole percent of a Lewis acid is present.

5. The process of claim 4 wherein from about 1 mole percent to about 10 mole percent of a Lewis acid is present.

6. The process of claim 1 wherein the temperature is from about 90° C. to about 150° C.

7. The process of claim 1 wherein a solvent selected from alkanes, cycloalkanes, aromatics, halogenated aromatics, (poly)glycols, (poly)glycol ethers, alkanols, alkyl carbonates or alkylene carbonates is additionally present.

8. The process according to claim 1 wherein the aromatic compound is selected from the group consisting of benzene, phenol, and methyl-, ethyl- or methoxy-substituted derivatives thereof.

9. The process according to claim 8 wherein the aromatic compound is toluene, xylene, mesitylene, phenol, methylphenol, methoxybenzene or 2,6-dimethylphenol.

* * * * *